United States Patent [19]

Kinard et al.

[11] Patent Number: 4,964,300

[45] Date of Patent: Oct. 23, 1990

[54] METHOD AND APPARATUS FOR DETERMINING TIME, DIRECTION AND COMPOSITION OF IMPACTING SPACE PARTICLES

[75] Inventors: William H. Kinard, Williamsburg; S. Fred Singer, Arlington, both of Va.; Jim J. Wortman, Chapel Hill, N.C.; Donald H. Humes, Hampton, Va.; Philip C. Kassel, Jr., Hampton, Va.; John E. Stanley, deceased, late of Wayne, N.J., by Marguerite Stanley, executrix

[73] Assignee: The United States of America as represented by the Administrator of the National Aeronautics and Space Administration, Washington, D.C.

[21] Appl. No.: 369,490

[22] Filed: Jun. 21, 1989

[51] Int. Cl.[5] .............................................. G01W 1/00
[52] U.S. Cl. ................................................ 73/170 R
[58] Field of Search ............. 73/170 R, 863; 340/601; 324/71.1, 71.4; 361/280

[56] References Cited

U.S. PATENT DOCUMENTS

| | | | |
|---|---|---|---|
| 2,944,250 | 7/1960 | Outt | 73/170 R |
| 3,159,029 | 12/1964 | Ruderman | 73/170 R |
| 3,238,774 | 3/1966 | Gurtler | 73/170 R |
| 3,277,724 | 10/1966 | Lundeberg | 73/170 R |
| 3,971,256 | 7/1976 | Zook et al. | 73/170 R |
| 4,237,736 | 12/1980 | Wright | 73/492 |

OTHER PUBLICATIONS

H. Fechtig et al., "Measurements of the Elemental and Isotopic Composition of Interplanetary Dust Collected on LDEF", R. H. Giese and P. Lamay (eds.), *Properties and Interactions of Interplanetary Dust*, 121–126 (1985), D. Reidel Publishing Co.

K. Rossler, "Laboratory Simulation of Chemical Interactions of Accelerated Ions with Dust and Ice Grains", R. Giese and P. Lamy, (eds.), *Properties and Interactions of Interplanetary Dust*, 357–363, 1985, D. Reidel Publishing Co.

*Primary Examiner*—Robert Raevis
*Attorney, Agent, or Firm*—George F. Helfrich; John R. Manning; Harold W. Adams

[57] ABSTRACT

A space particle collector for recording the time specific particles are captured, and its direction at the time of capture, utilizes an array of targets, each comprised of an MOS capacitor on a chip charged from an external source and discharged upon impact by a particle through a tab on the chip that serves as a fuse. Any impacting particle creates a crater, but only the first will cause a discharge of the capacitor. A substantial part of the metal film around the first crater is burned off by the discharge current. The time of the impulse which burns the tab, and the identification of the target, is recorded together with data from flight instruments. The metal film is partitioned into pie sections to provide a plurality of targets on each of an array of silicon wafers, thus increasing the total number of identified particles that can be collected. It is thus certain which particles have been captured at what specific times.

8 Claims, 4 Drawing Sheets

METHOD AND APPARATUS FOR DETERMINING TIME, DIRECTION AND COMPOSITION OF IMPACTING SPACE PARTICLES

ORIGIN OF THE INVENTION

The invention described herein was jointly made by employees of the United States Government and contract employees in the performance of work under a NASA Contract and is subject to the provisions of Public Law 96-517 (35 U.S.C. 202) in which the contractor has elected not to retain title.

TECHNICAL FIELD

This invention relates to collecting space particles for laboratory analysis using a collector, and more particularly to a method and apparatus for recording the time a specific particle is collected, and for recording data sufficient to allow the direction of the particle at the time of collection.

BACKGROUND ART

A Long Duration Exporation Facility (LDEF) was deployed by Space Shuttle (STS-13) in Apr., 1983, for science and technology experiments. One of several experiments aboard LDEF was designed to collect dust particles in near earth space for laboratory analysis of elemental and isotopic compositions. Additional information for which the experiment was designed included the flux and size distribution of micrometeroids. (H. Fechtig, et al., "Measurements of the Elemental and Isotopic Composition of Interplanetary Dust Collected on LDEF," R.H. Giese and P. Lamay (eds.), *Properties and Interactions of Interplanetary Dust*, 121–126 (1985).

The cells used by H. Fechtig, et al., to collect dust particles aboard LDEF consisted of Ge target plate (substrate) and a 2.5 μm thick plastic (Mylar) foil separated from the substrate by 0.2 mm. To prevent erosion of the plastic by atomic species present in space at orbital altitudes, the foil was coated with 100 Å Au/Pd and 800 Å or Ta on the inside. The materials used were chosen for their chemical purity and their mechanical and thermal properties. Particles impacting the foil at velocities ~ 10 km/sec break up, melt or vaporize during penetration of the foil and subsequent impact on the Ge. The resulting residues deposited on substrate and the Ta coated inside surface of the foil were then to be analyzed upon recovery of the LDEF.

While this prior work was intended to fulfill a need to study the elemental and isotopic compositions of residues resulting from micrometeroids, it does not allow for the identification of the source of the dust particles. It would be important in studies of micrometeroids and space debris to not only identify the comets from which particle residue is collected, but to also identify man made space dust and determine its movement in near earth space. For example, studies of the orbital dynamics of $Al_2O_3$ particles produced by firing solid propellant rocket motors in space require that the time, the point in space, and the direction of impact be determined.

The point in space may be determined from the orbital position of the LDEF at the moment of impact, but that requires recording the precise time particles impact. There are a number of techniques that may be used to determine the precise time that particles impact targets in space, for example, by using acoustic or capacitor type detectors. However, if more than one impact has occurred on a target simultaneously, these techniques will not allow an impact time to be associated with each of the resulting craters for further analysis. Another technique for determining impact time involves controlling the time a target area is exposed in space, thus assuring that any crater observed in a given target area occurred during the time that area was exposed. A roll of target material which is slowly advanced across an exposure window is one specific method of controlling the exposure time. However, this technique can not establish the precise time of impact. It can establish only that it occurred in a time interval during which the point of impact on the scrolling film was exposed, which is usually several days.

There exists no prior art which can assure determining the precise time a given crater is formed when multiple craters are present on a target in order to determine the direction of the impacting particles. As noted above, precise impact times can be measured with microphones or conventional capacitor type impact detectors, but the various craters are not identified with the times of impact. Consequently, it is not possible to later analyze the craters to determine the direction of each particle. The impact time resolution using the conventional time-of-exposure exposure technique is not sufficient to relate observed craters to specific sources of particles by determining their direction. Also the various equipment necessary to control time of exposure are heavy, bulky, and complex thus making them costly for space operations.

STATEMENT OF THE INVENTION

In accordance with the present invention, apparatus is provided on a spacecraft to establish time, direction, and composition of impacting space particles. The impact time on a target is recorded and directly related to a particular crater. The direction of the particle motion relative to the target is determined from the orientation of the target on the spacecraft in its orbital path at the recorded time of impact. Through post flight laboratory analysis it is possible to establish the point and direction in space of each impacting particle so that when the composition of the particle from the residual material in the crater is analyzed, it is known what the space trajectory of the particle was.

A preferred embodiment of the target is comprised of a metal-oxide-semiconductor (MOS) capacitor, such as an n-MOS capacitor comprised of an n-doped silicon substrate, an $SiO_2$ layer grown on the substrate and a metal film. An electrical circuit is connected from the metal film (front capacitor plate) to an ohmic contact on the substrate (second capacitor plate). The circuit includes means having a fuse for maintaining a charge on the capacitor until it is discharged upon impact by a particle which produces a temporary conducting path between the metal front plate and the silicon substrate. With the proper relationship set between the stored capacitor energy and the thickness of the front metal plate, the current density in the conducting path will burn a substantial region of the front plate around the crater. When the attached charge circuit means attempts to recharge the capacitor, the recharge current will be sufficient to burn the fuse and thus prevent recharging. Any particle impact which may thereafter occur will not result in burning (removing) metal around its crater, as a consequence of which the time recorded of the discharge current pulse can be associated with the only burned out crater in the target. The electrical circuit also includes means for recording orientation data of the target vehicle in space at the time or impact, from which the direction of the impacting particle may be determined upon later analysis.

To achieve multiple impact detection, multiple MOS capacitors may be arrayed, and to further increase the number of capacitors, the metal for the front plate of each may be deposited in sections to define a plurality of distinct capacitors on each MOS substrate wafer. Thus in a second embodiment of the present invention a masked front metal plate is deposited on a single MOS wafer in order to divide the MOS wafer area A into a number N of individual capaciors, each with its own fuse for connection to the charging means, and each with its own means for providing an identification code to be recorded at the time of capacitor discharge. Due to the fact that only one impact can be recorded per capacitor, the total number of recorded impacts on a MOS wafer of area A is increased by a factor N without any increase in the area A.

DETAILED DESCRIPTION OF THE INVENTION

The invention records the time a single crater is formed in each exposed target, and records data on the orientation of the impacted target to allow the direction of the particle (relative to the target at the time of impact) to be established. After recovery of the targets from space, the composition of each particle can be determined through post-flight laboratory analysis of the residual material in each crater. The collected dust particles from different sources in space can be studied with the related composition, impact time and impact direction data. For example, the unique compositions of particles from various comets can be studied. The present invention will also allow craters resulting from man made space dust to be identified, such as particles of $Al_2O_3$ which are produced by firing a solid propellant rocket motor in space.

Particles occurring naturally in space may be species with high kinetic energies from, for example, comet tails, instellar grains, and particle collisions. These naturally occurring particles have mass densities from 1 to 10 g cm$^{-3}$ and are primarily composed of the abundant elements H, C, N, O, Ca, Mg, Si, S and Fe. Studies of the orbital dynamics of these species of dust particles can also be made with data from the present invention.

Figure 1A:
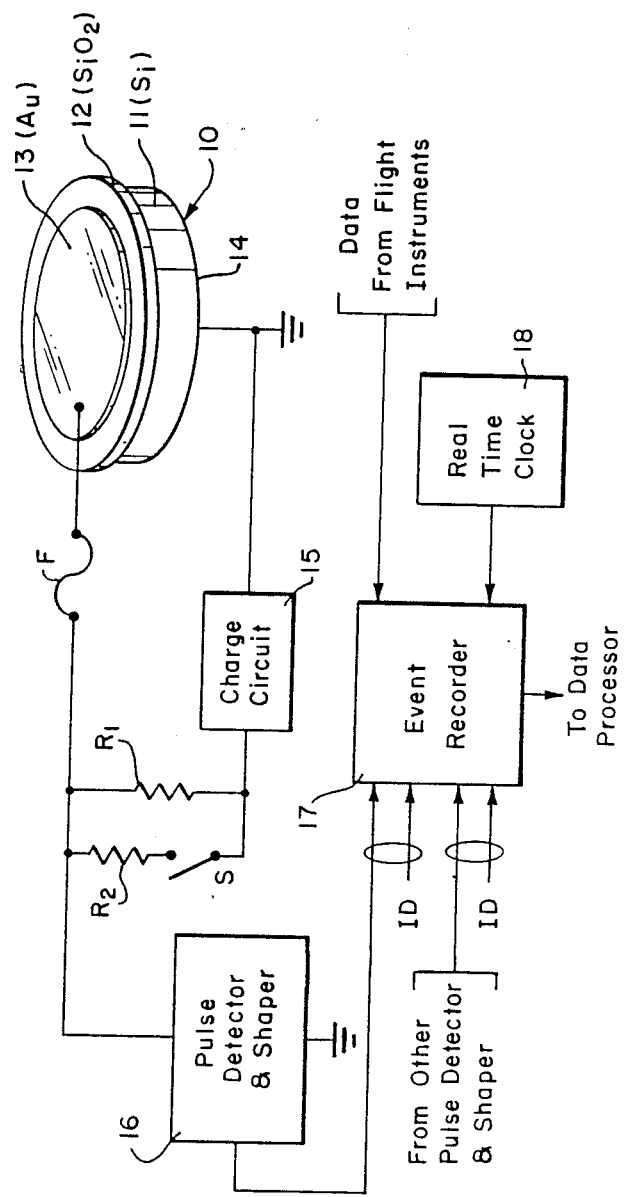
FIG. 1a is a schematic diagram, partially in functional block form, illustrating the concept of the invention.
Figure 1B:
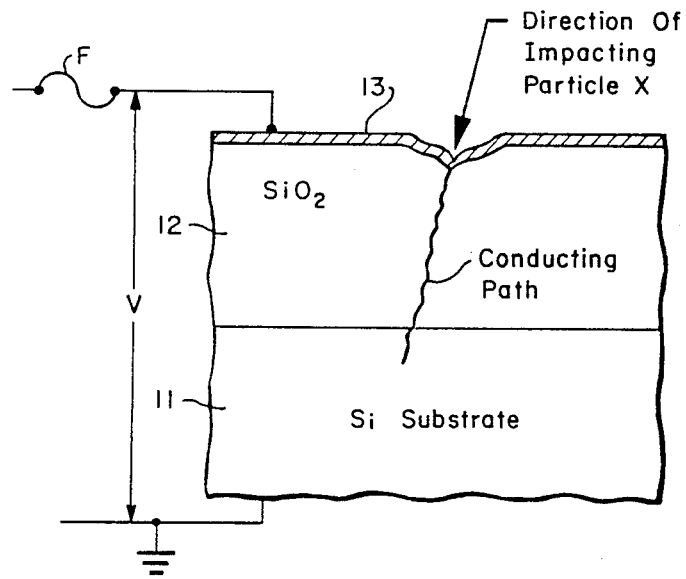
FIG. 1b is a cross section of a part of the MOS capacitor structure showing a conductive path through the dielectric $SiO_2$ caused by impact of a dust particle.
Figure 1C:
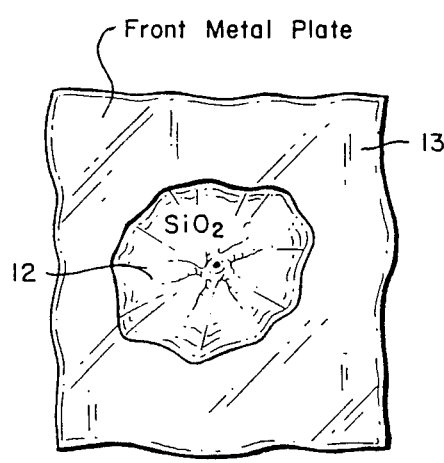
FIG 1c is a plan view illustrating the burned out metal in the cavity around the point of impact of the particle shown in FIG. 1b, and illustrating a crater caused by impact of a subsequent particle.

Referring to FIG. 1a, a MOS capacitor 10 is comprised of a substrate 11 that is n-doped, a layer 12 of $SiO_2$ grown on the substrate, a front metal plate 13 vapor deposited on the $SiO_2$ layer, and a back metal plate 14. The MOS capacitor is initially charged by a circuit 15 through a current limiting resistor $R_1$ and fuse F. Once the initial charge has been placed on the MOS capacitor 10 it is ready to detect impact of a particle. A shunt switch S is then closed to effectively place a second resistor $R_2$ in parallel with the current limiting resistor, so that once a hyper-velocity particle impacts the MOS capacitor 10 in space, and the particle produces a crater in the target through the front metal plate, a temporary high current conducting path is provided through the oxide layer, as shown in FIG. 1b, that initiates a capacitor discharge process. With the proper relationship between the resistors $R_1$ and $R_2$ in parallel, stored capacitor energy V, and the thickness of the front metal plate 13, the current density will be sufficient to burn out the metal plate 13 from a substantial region surrounding the impact crater as shown in FIG. 1c.

When the charge circuit 15 attempts to recharge the MOS capacitor 10 with the current limiting resistor $R_1$ in parallel with the resistor $R_2$, the surge of recharge current will be sufficient to blow the fuse F, thus preventing the capacitor from being recharged, and therefore preventing it from being used again to record a second particle impact. Any particle impact occurring when the capacitor 10 is uncharged will produce a crater, but will not result in any discharge current, and therefore will not remove metal from around the crater. Instead only a crater surrounded closely by metal will be formed. Subsequent craters thus formed are readily distinguished from an initial crater. In that manner a recorded time for the initial crater can be related to the time of impact of the particle producing the burned out crater, even though particles later impact the MOS capacitor.

Figure 2:
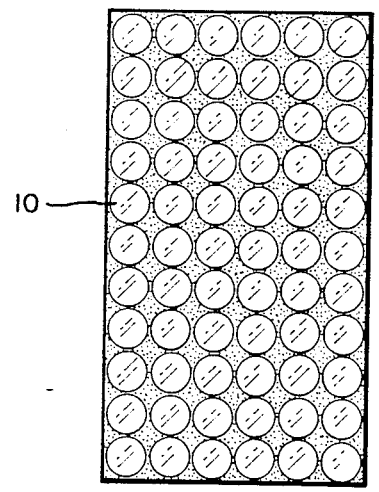
FIG. 2 illustrates an array of MOS capacitors, each connected as the one shown in FIG. 1 to an event recorder and real time clock.

The direction of particle impact is established using recorded data of the location and orientation of the space vehicle at the time of impact. To accomplish that, the discharge current pulse is detected by a pulse detector and shaper 16, which in turn triggers an event recorder 17 to record the capacitor identification code, and the time at that moment from a real time clock 18, together with data from flight (altitude or orientation) control instruments. Trigger pulse and capacitor ID inputs from other capacitors are connected to the event recorder to accommodate a plurality of MOS capacitors as shown in FIG. 2. Post flight analysis of the recorded data and the material remaining in the burned out crater of each MOS capacitor establishes the direction and the composition of the particle.

The basic principle of the present invention is the creation if a one time temporary conducting path in the $SiO_2$ dielectric of the MOS capacitor by an impacting particle. Silicon dioxide $SiO_2$ has a low carrier concentration compared with other dielectric materials, such as $Si_3N_4$ or $Al_2O_3$. Therefore conductivity for a given electric field is the lowest in $SiO_2$. Carriers (holes and electrons) can be generated by disrupting the valence bonds of some atoms in the $SiO_2$ crystal structure by a hypervelocity particle passing through it.

The precise mechanism for creating this temporary conduction path is belived to be a result of Auger recombination processes after the thermal-equilibrium condition of the $SiO_2$ layer is disturbed by the kinetic energy of the hypervelocity particle passing through it, leaving a trail of ionized atoms. The bond-to-bond recombinations of electron-hole pairs that produce the temporary conduction path are made possible by transfer of the recombination energy to another free electron or hole.

Another mechanism believed to be contributing is the presence of impurities momentarily added by an impacting particle with more (or less) valence electrons in the $SiO_2$ lattice to produce carriers (electrons or holes). For example, substitution of one Si atom (four valence electrons) by one P atom (five valence electrons) results in a donation of one negative charge (electron) in the $SiO_2$ lattice. Similarly positive charges (holes) are produced in the $SiO_2$ lattice by substitution of one Si atom by one atom of an element with fewer valence electrons, such as Al (three valence electrons). Thus, a penetrating particle of some element may introduce a trail of impurities in the $SiO_2$ layer, creating a semiconductor (donor or acceptor) path. This semiconductor path will then aid the rapid discharge of the capacitor.

The discharge current is highly concentrated at the point of particle impact and will therefore cause some of the metal plate around the point of impact to burn off due to excess current in the same way a fuse burns out. The control on this burning off of metal is the submicron thickness (approximately 1 $\mu$m) of the vapor-deposited front metal (gold) plate.

The charge circuit 15 is capable of maintaining a charge on the capacitor until it is discharged by an impacting particle. When the charge circuit attempts to recharge the capacitor with the shunt switch S closed, the surge of charging current will burn out the fuse F. As a consequence, the capacitor is not charged sufficiently to produce enough current to burn out a crater of any other particle that may impact the capacitor; only the first particle impact after initial charge will produce a discharging pulse of current which is detected by a pulse detector and shaper 16.

The output pulse from the pulse detector and shaper 16 triggers the event recorder 17, which is then caused to record the identification number (ID) of the capacitor (which in practice will be one of many in an array) and the time of impact as measured by a real time clock 18, as noted hereinbefore. Only one particle impact will thus be recorded for a capacitor during a single instrument flight. Before it can be used again, the fuse F must be replaced. At that time, the front plate of the capacitor should also be repaired. Alternatively the old burned out crater may be marked in order to identify it as having been previously analyzed. Then another initial charge is placed on the capacitor through the current limiting resistor R with the switch S open.

In practice, an array of many capacitors will be connected to the event recorder 17, and the event recorder will respond to each impact detected to store the event and the capacitor ID, as noted hereinbefore. To facilitate this, the event recorder may consist of a plurality of memory locations, each addressed by a different ID code. Alternatively, a plurality of registers may be provided numbered 1 through N, one for each capacitor identified by the numbers 1 through N. A connection is provided from a separate pulse detector of each capacitor in the array to a trigger input terminal of a separate register of corresponding number. The event pulse received over this connection causes the register to store the time from the real time clock 18, and to also store data from flight instruments. In that way two or more capacitors may be impacted simultaneously, and each will be recorded separately. If the event recorder is implemented with an addressable memory, only one of two simultaneous impacts can be recorded. Where that would be sufficient, some saving in cost and space could be realized. But in either case, space may be saved by implementing the pulse detector, fuse F, and switch S as an integrated circuit on the silicon substrate of each capacitor. Even the resistors $R_1$ and $R_2$ could be included in that integrated circuit.

Figure 3A:
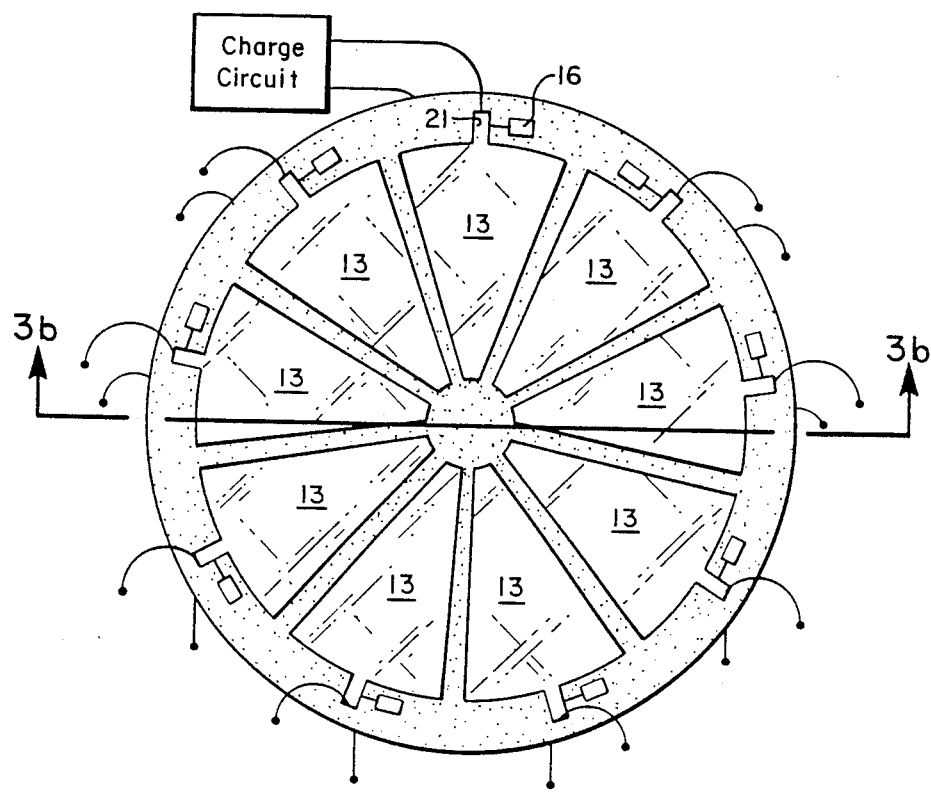
FIGS. 3a and 3b illustrate the manner in which each MOS capacitor illustrated in FIG. 2 may be divided into a plurality of pie-shaped capacitors by use of a proper mask in the final step of fabrication of the MOS capacitors on a wafer, namely the step of depositing the metal front capacitor plate.

To provide a plurality of MOS capacitors, each wafer of an array may be divided into a plurality of capacitors, as illustrated in FIG. 3a for one silicon wafer constructed as before with an $SiO_2$ layer 12 grown over a silicon substrate 11, but with the front plate 13 vapor deposited through a mask to produce eight pie-shaped front plates 13, each with a tab 21 to which the charge circuit is connected. The back plate for the capacitors comprised of the eight pie shaped front plates 13 may be comprised of the entire silicon substrate 11, preferably with the metal film 14 in ohmic contact over the entire back side.

The tab 21 of each pie plate constitutes the fuse F, and each fuse is connected to an integrated circuit pulse detector and shapers 16.

Figure 3B:
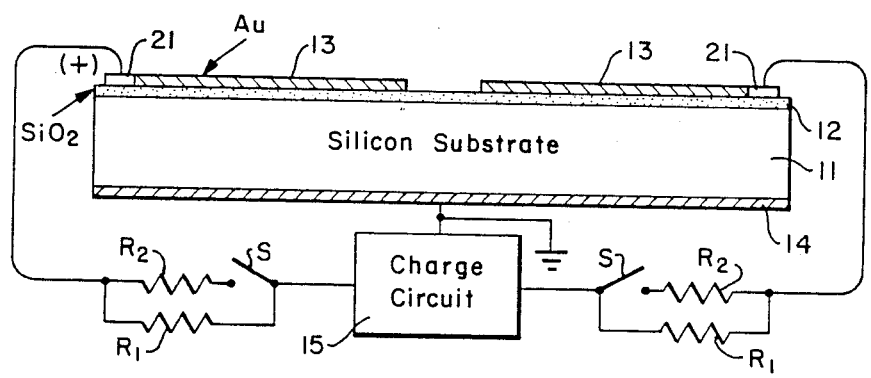
Figure 4:
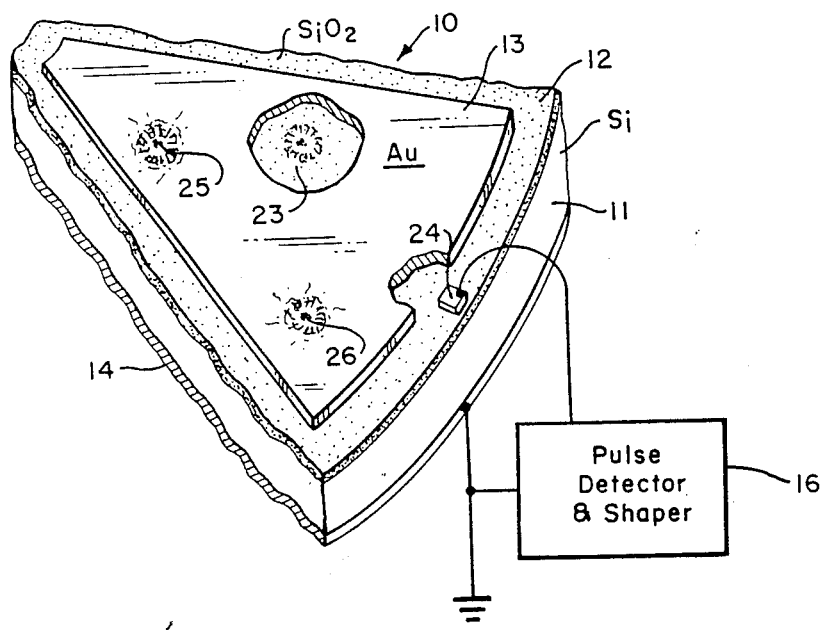
FIG. 4 illustrates a pie-shaped capacitor of FIG. 3a after a particle impact has discharged it, and a surge of recharging current has burned out its fuse tab.

FIG. 3b illustrates in a cross section taken along a line b—b in FIG. 3a the manner in which each pie-shaped capacitor of a wafer is separately connected to the charge circuit through its own tab (fuse) 21. FIG. 4 illustrates a pie-shaped capacitor from the wafer of FIG. 3a with a burned out crater 23 produced by a first particle impact, and a tab (fuse) 21 burned out by a surge of recharging current. Also shown are craters 25 and 26 caused by particles compacting the front plate of the capacitor after the initial particle impact.

Although preferred embodiments of the invention have been described and illustrated herein, it is recognized that modifications and equivalents may readily occur to those skilled in the art, particularly in the selection of materials. Consequently, it is intended that the claims be interpreted to cover such modifications and equivalents.

We claim:

1. In a method for collecting particles from space using a particle collector comprised of a metal-oxide-semiconductor capacitor having a thin-film metal plate, an oxide insulating layer, and a semiconductor substrate as a second plate, and having a circuit for charging said capacitor through, said capacitor having its metal plate exposed to space, whereby particles impacting said metal plate penetrate through the oxide insulating layer to the semiconductor substrate where they are retained, the steps of initially charging said capacitor from a current source through a high impedance path and a fuse and maintaining said charge through a path lower impedance than said high impedance path and said fuse, whereupon discharge of said capacitor through a momentary conduction path is created by said penetrating particle in its penetration path to the substrate, thereby melting away metal of said thin-film plate around a crater created by the impacting particle, and recharge current from said current source melts away said fuse to open the current path for recharging the capacitor and detecting for recordation the real time of the capacitor discharge, whereby any particle which may subsequently impact will not cause a discharge path, and may be readily distinguished by not having metal melted away from the crater.

2. In a method as defined in claim 1, the further step of recording orientation and position data concerning the particle collector along with the time of said capacitor discharge.

3. In a method as defined in claim 2, where a plurality of capacitors, each being similar to the metal-oxide-semiconductor capacitor, are employed in an array, each capacitor with its own initial charge and charge maintenance paths through a fuse, the further steps of recording for each capacitor the real time each capacitor discharges, together with a unique identification code for each capacitor that discharges and the orientation and position data.

4. In a method as defined in claim 3, increasing the number of particles that may be captured for analysis by dividing each thin-film metal plate into a plurality of segments, and providing for each said segment a circuit for the initial charge, maintenance of charge and discharge recording capability as if for each capacitor, whereby a plurality of said segments share the same oxide and semiconductor substrate.

5. Apparatus for collecting particles from space comprising an MOS capacitor having a thin-film metal plate exposed to space, an oxide layer, and a substrate serving as a second plate of said capacitor, circuit means for charging said capacitor through a high impedance path and a fuse, and for maintaining said charge through a low impedance path and said fuse, means for detecting discharge of said capacitor upon impact of a first particle from space, and means responsive to the detection of discharge for recording the real time of impact, whereby discharging current melts away said thin-film metal around the crater produced by the first particle to impact, and recharging current melts away said fuse to prevent any charge and discharge for subsequent particles so that craters produced by subsequent particles may be distinguished by not having thin-film metal melted away.

6. Apparatus as defined in claim 5 including means for storing orientation and position data for the apparatus at the time of discharge.

7. Apparatus as defined in claim 6 including a plurality of capacitors in an array, each capacitor being similar to the MOS capacitor, each with its own fuse, initial charge and charge maintenance circuits and discharge detection means, wherein said recording means includes means for separately recording the time of discharge of each capacitor with identification of the discharging capacitor.

8. Apparatus as defined in claim 7 wherein each of a number M capacitors arrayed has its thin-film metal plate divided into a number N plurality of segments, thereby providing N segmented capacitors, and each segmented capacitor is provided with initial charging and charge maintenance circuits, discharge detection means, and recording means, thereby increasing the number of particles collected and identified for analysis by a factor of N to a total of NM.

* * * * *